(12) United States Patent
Sjostedt et al.

(10) Patent No.: US 7,910,351 B2
(45) Date of Patent: Mar. 22, 2011

(54) MUTANT F. TURLARENSIS STRAIN AND USES THEREOF

(75) Inventors: Anders Sjostedt, Umea (SE); Joseph Wayne Conlan, Ottawa (CA)

(73) Assignee: National Research Council of Canada, Ottawa (CA)

( * ) Notice: Subject to any disclaimer, the term of this patent is extended or adjusted under 35 U.S.C. 154(b) by 371 days.

(21) Appl. No.: 11/918,648

(22) PCT Filed: Apr. 19, 2006

(86) PCT No.: PCT/CA2006/000621
§ 371 (c)(1),
(2), (4) Date: Jan. 28, 2008

(87) PCT Pub. No.: WO2006/111019
PCT Pub. Date: Oct. 26, 2006

(65) Prior Publication Data
US 2009/0098163 A1   Apr. 16, 2009

(30) Foreign Application Priority Data

Apr. 20, 2005   (CA) .................................... 2502999

(51) Int. Cl.
C12N 1/12   (2006.01)
(52) U.S. Cl. ................ 435/252.1; 435/172.1; 424/234.1; 536/23.7
(58) Field of Classification Search ........................ None
See application file for complete search history.

(56) References Cited

FOREIGN PATENT DOCUMENTS
WO   WO 2004/003009 A2   1/2004

OTHER PUBLICATIONS

Twine, S. et al. A mutant of Francisella tularensis strain SCHU S4 lacking the ability to express a 58-kilodalton protein is attenuated for virulence and is an effective live vaccine. Infection and immunity, Dec. 2005, vol. 73, No. 12, pp. 8345-8352.
Broekhuijsen, M. et al. Genome-wide DNA microarray analysis of Francisella tularensis strains demonstrates extensive genetic conservation within the species but identifies regions that are unique to the highly virulent F. tularensis subsp. tularensis. Journal of Clinical Microbiology, Jul. 2003, vol. 41, No. 7, pp. 2924-2931.
Svensson, K. et al. Evolution of subspecies of Francisella tularensis. Journal of Bacteriology, Jun. 2005, vol. 187, No. 11, pp. 3903-3908.
Larsson, P. et al. The complete genome sequence of Francisella tularensis, the causative agent of tularemia. Nature Genetics, Feb. 2005, vol. 37, No. 2, pp. 153-159.
Sjostedt, A. Virulence determinants and protective antigens of Francisella tularensis. Curr Opin Microbiol 2003; 6:66-71.
Eigelsbach, H.T. et al. Prophylactic effectiveness of live and killed tularemia vaccines I. Production of vaccine and evaluation in the white mouse and guinea pig. J Immunol 1961; 87:415-25.
Saslaw, S. et al. Tularemia vaccine study II. Respiratory challenge. Arch Int Med 1961; 107:702-14.
Saslaw, S. et al. Tularemia vaccine study I. Intracutaneous challenge. Arch Int Med 1961; 107:689-701.
Burke, D.S. Immunization against tularemia: Analysis of the effectiveness of live Francisella tularensis vaccine in prevention of laboratory-acquired tularemia. J Infect Dis 1977; 135(1):55-60.
Conlan, J.W. 2004. Vaccines against Francisella tularensis—past, present and future. Expert Review of Vaccines. 3:307-314.
Eigelsbach, H.T. et al. Aerogenic immunization of the monkey and guinea pig with live tularemia vaccine. Proc. Soc Exptl Biol Med 1961; 108:732-34.
Hornick, R.B. et al. Aerogenic immunization of man with live tularemia vaccine. Bact Revs 1966; 30(3):532-38.
Conlan, J.W. et al. Aerosol-, but not intradermal-immunization with the live vaccine strain of Francisella tularensis protects mice against subsequent aerosol challenge with A highly virulent type A strain of the pathogen by an $\alpha\beta$ T cell- and interferon gamma-dependent mechanism. Vaccine 2005; 23:2477-2485.
Johansson, A. et al. Evaluation of PCR-based methods for discrimination of Francisella species and subspecies and development of a specific PCR that distinguishes the two major subspecies of Francisella tularensis. J Clin Micro 2000; 38(11):4180-85.
Golovliov, I. et al. A method for allelic replacement in Francisella tularensis. FEMS Microbiol Lett 2003; 222 (2):273-280.
Conlan, J.W. et al. Experimental tularemia in mice challenged by aerosol or intradermally with virulent strains of Francisella tularensis: Bacteriologic and histopathologic studies. Microb Pathog 2003; 34:239-48.
Golovliov, I. et al. Identification of proteins of Francisella tularensis induced during growth in macrophages and cloning of the gene encoding a prominently induced 23-kilodalton protein. Infect Immun 1997; 65(6):2183-2189.
Lai, X. et al. Expression of IgIC is necessary for intracellular growth and induction of apoptosis in murine macrophages by Francisella tularensis. Microbial Pathogenesis 2004; 37:225-30.
Lindgren, H. et al. Factors affecting the escape of Francisella tularensis from the phagolysosome. J Med Micro 2004; 53:953-958.
Lauriano, C.M. et al. MgIA regulates transcription of virulence factors necessary for Francisella tularensis intraamoebae and intramacrophage survival. PNAS 2004; 101(12): 4246-4249. Database UniProt [Online], "SubName:Full=Putative uncharacterized protein", Feb. 1, 2005, XP002526472 retrieved from EBI accession No. UNIPROT:Q5NGC7, Database accession No. G5NGC7.
Database Geneseq [Online], "Francisella tularensis immunogenic protein 61, SEQ ID No. 61", Mar. 25, 2004, XP002526473 retrieved from EBI accession No. GSP:ADH12880, Database accession No. ADH12880.
Rohmer, Laurence et al., "Potential source of Francisella tularensis live vaccine strain attenuation determined by genome comparison", Infection and Immunity, vol. 74, No. 12, Dec. 2006, pp. 6895-6906, XP002526471, ISSN: 0019-9567.
EP 06 72 1840 Supplementary Search Report, Jun. 8, 2009.

*Primary Examiner* — Jennifer E Graser
(74) *Attorney, Agent, or Firm* — Johanna Coutts

(57) ABSTRACT

A mutant strain of Francisella tularensis has attenuated virulence and has a mutation in the gene coding for a putative peroxynitrite resistance protein A (prpA) which prevents normal function of the protein. The mutant is useful as a vaccine against type A and B virulent strains of F. tularensis, and is produced by obtaining a virulent F. tularensis strain and mutating the gene, FTT0918, that codes for prpA.

14 Claims, 2 Drawing Sheets

MUTANT *F. TULARENSIS* STRAIN AND USES THEREOF

FIELD OF THE INVENTION

The invention relates to attenuated *F. tularensis* useful as live vaccines against tularemia in humans and other mammals.

BACKGROUND OF THE INVENTION

*Francisella tularensis* is a pathogenic intracellular bacterium capable of causing infectious disease in more than 150 mammalian species. Arthropod vectors, such as ticks, flies and mosquitoes, are frequently involved in the transmission of the pathogen to mammals but it can be transmitted also via contaminated food and water, and aerosols. There are four subspecies of *F. tularensis*, but only two, subspecies *tularensis* (type A), and subspecies *holarctica* (type B), are commonly infectious for humans. Only type A strains of *F. tularensis* may cause lethal infection in humans, in particular untreated respiratory tularemia has a high mortality rate if left untreated.

Because of its high infectivity, ease of dissemination by aerosol, and capacity to cause severe morbidity and mortality, type A *F. tularensis* has long been considered a potential biological warfare agent. However, to date no specific virulence factors that explain the high virulence of type A strains have been identified. A comparative genomic analysis showed that the proportion of genes conserved among the four subspecies of *F. tularensis* is high, >97%, and that less than 30 of a total of 1,800 genes are unique to type A versus type B *F. tularensis*.

Live attenuated *F. tularensis* vaccines were developed in Russia in the 1950's from a type B strain. One of these strains, designated as the live vaccine strain, LVS, was transferred to the US. Vaccine studies conducted on volunteers in the 1960's demonstrated that it protected humans against systemic inoculation or inhalation of a type A strain of the pathogen. Epidemiological studies of tularemia cases among *Francisella* researchers before and after the introduction of LVS vaccination confirmed its utility. However, despite having been developed almost 50 years ago, the nature of the genetic lesion responsible for its attenuation, the protective antigens, and the immunological basis for its efficacy remain unknown.

Moreover, in both human and animal studies, systemic vaccination with LVS provided sub-optimal protection against aerosol challenge with type A *F. tularensis*. For these reasons, LVS has never been licensed as a vaccine. In the past, it was granted investigational new drug (IND) status, but this was revoked by the FDA several years ago. These problems with LVS have motivated a search for better-defined vaccines of equal or greater efficacy.

Because the protective protein antigens of *F. tularensis* are completely unknown, a sub-unit vaccine is currently inconceivable, especially as it would need to be formulated with an adjuvant system able to elicit robust $CD4^+$ and $CD8^+$ T cell responses, both of which are known to be required to control tularemia. Although experimental adjuvants with these properties exist, none have yet been approved for clinical use.

The identities and characteristics of the virulence factors and protective antigens of the subspecies of *Francisella* are essentially unknown. Although recent comparative genomics analyses have begun to demonstrate genetic differences among the subspecies, these alone have been insufficient to explain their relative virulence. Moreover, it is known that sublethal infection of mice with subspecies *novicida* fails to confer protection against subsequent challenge with subspecies *holarctica* or *tularensis* suggesting that the protective antigens are highly restricted. It has also been observed that only certain mouse strains can be protected by LVS. On this basis, it seems unlikely that defined mutants of the *holarctica* subspecies would be more effective vaccines than LVS.

Thus, it would be desirable to generate a defined type A strain mutant lacking the minimum number of genes required to render it a safe and effective live vaccine. However, no successful strategy has been disclosed in the prior art.

SUMMARY OF THE INVENTION

A first object of the present invention is to provide mutant *Francisella tularensis* cells that have attenuated virulence and a mutated FTT0918 gene encoding for a putative peoroxynitirite resistance protein (prpA) such that the cells are substantially lacking functional prpA. These cells are useful as vaccines in that they provide protection in immunized humans and other mammals against virulent type A and B strains of *F. tularensis*.

A further object of the invention is to provide for a method of obtaining mutant *F. tularensis* cells for use as a vaccine. Virulent *F. tularensis* cells are treated to delete or mutate the FTT0918 gene, then viable mutant cells substantially lacking in functional prpA are selected and isolated.

A further object of the invention is to provide for a method for immunizing humans or other mammals against virulent type A and B strains of *F. tularensis*. The subject human or mammal is inoculated with the mutant *F. tularensis* lacking prpA function, resulting in a reduced susceptibility to virulent *F. tularensis*.

A first aspect of the invention provides for a mutant of *Francisella tularensis* that has attenuated virulence and that has a mutation in the nucleotide sequence that encodes FTT0918.

A further aspect of the invention provides for a mutant of *Francisella tularensis* wherein the nucleotide sequence that encodes the putative peroxynitrite resistance protein A (prpA) in wild-type *Francisella tularensis* is mutated, resulting in attenuated virulence.

A further aspect of the invention provides for an immunogenic composition or vaccine comprising a mutant of *Francisella tularensis* that has attenuated virulence and that has a mutation in the nucleotide sequence FTT0918, and a pharmaceutically acceptable diluent, carrier, vehicle or excipient.

A further aspect of the invention provides for a method of producing a mutant of *Francisella tularensis* that has attenuated virulence and that has a mutation in the nucleotide sequence FTT0918, comprising the steps of obtaining cells of a virulent *F. tularensis* strain; mutating the nucleotide sequence FTT0918; selecting for viable cells with attenuated virulence and FTT0918 mutations; and isolating said cells with attenuated virulence and FTT0918 mutations.

A further aspect of the invention provides for a method of producing a mutant of *Francisella tularensis* that has a mutation in the nucleotide sequence that encodes the putative peroxynitrite resistance protein A (prpA) in wild-type *Francisella tularensis*, resulting in attenuated virulence, comprising the steps of obtaining cells of a virulent *F. tularensis* strain; mutating the nucleotide sequence that encodes prpA; selecting for viable cells with attenuated virulence and mutations in the nucleotide sequence that encodes prpA; and isolating said cells with attenuated virulence and mutations in the nucleotide sequence that encodes prpA.

DETAILED DESCRIPTION OF THE INVENTION

Figure 1:
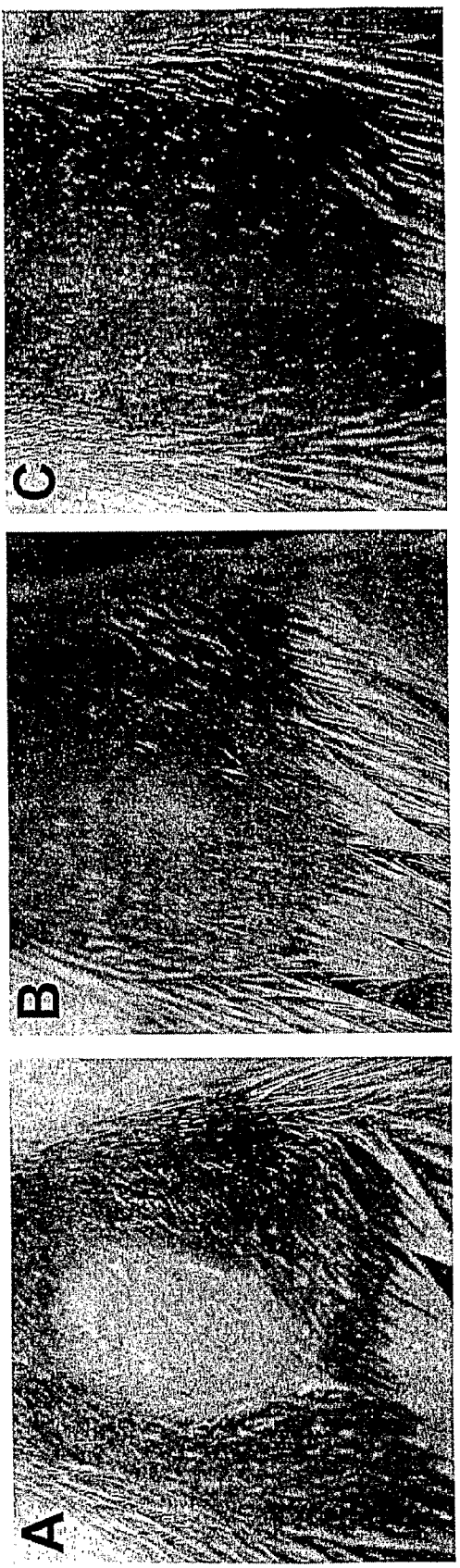
FIG. 1 illustrates skin lesion development at sites of intradermal inoculation of *F. tularensis* strains. Representative skin reaction observed in mice inoculated with A, $10^2$ CFU of SCHU S4 or $10^6$ CFU LVS; B, $10^2$ CFU 12A or $10^6$ SCHU AV; C, nothing or $10^2$ CFU LVS or $10^6$ CFU mutant ΔigIC.

While possible *F. tularensis* vaccines have been explored in the prior art, the genetic mutations responsible for attenuation have not been identified. Further, vaccines such as LVS (live vaccine strain) have not proven to be efficacious under all circumstances, such as aerosol challenge by type A *F. tularensis*. In addition, LVS causes an obvious skin reaction at the site of inoculation in the skin (FIG. 1), which is undesirable. Others have examined spontaneously mutated type A strains as live vaccines in the past, but concluded they were more virulent than LVS, and not therefore suitable for this purpose. Accordingly, a better understanding of the genetic mutations causing *F. tularensis* attenuation is needed. In addition, an efficacious and safe *F. tularensis* vaccine is required.

In order to explore the genetic mutations responsible for attenuated virulence, two mutant strains of *F. tularensis*, FSC043/SCHU AV and LVS, were analysed. One such mutation was found to be in the gene FTT0918 which encodes a putative peroxynitrite resistance protein A (prpA). The identification of this gene is a significant step towards developing a safe and efficacious vaccine for *F. tularensis*, as it is now possible to create mutants in which the gene is intentionally mutated.

A *F. tularensis* strain mutant ΔFTT0918 (deposit Accession No. CCUG 59671) is the foundation strain for a new defined live vaccine against tularemia. It will be understood that one or a few additional genes may also be deleted or mutated. Although spontaneous mutants of *F. tularensis*, mostly notably LVS, have been used as live vaccines already, it is not obvious that the absence of gene FTT0918 was responsible for the attenuation of this strain since it lacks several additional genes present in clinical type B strains. Further, it is shown that the mutant strain is effective as a vaccine, in that mice inoculated with the mutant survived both intradermal and aerosol challenges with virulent type A *F. tularensis*.

Identification of Genetic Mutations Responsible for Attenuation

A spontaneous mutant with attenuated virulence, designated FSC043 or SCHU AV (hereinafter referred to as SCHU AV), of *Francisella tularensis* subsp. *tularensis* is known. The virulence of the mutant is severely attenuated; its intradermal $LD_{50}$ in mice was >$10^8$ CFU compared to <10 CFU for SCHU S4. SCHU AV proteins were compared with those of the wild-type strain, SCHU S4, a prototypic strain known to be highly virulent for humans and multiple species of experimentally infected mammals including mice. It was demonstrated by proteomic analysis that SCHU AV expressed several proteins at significantly different levels than the wild-type strain, SCHU S4.

A proteomic comparison of SCHU AV and the wild type virulent parental strain, SCHU S4, revealed the absence or lower expression of 9 proteins from the former versus latter (Table 6). Intriguingly, SCHU AV and LVS expressed a specific protein (spot 35 in FIG. 2 panel b) not expressed by the parental strain. Proteomic analysis of this protein revealed it to be a hybrid protein consisting of the N-terminal domain of one wild-type protein encoded by gene FTT0918 and the C-terminal domain of another encoded by gene FTT0919. A genomic analysis confirmed the presence of the hybrid gene responsible for this fusion protein in both spontaneous mutants LVS and SCHU AV.

Analysis of Role of ΔFTT0918 and ΔFTT0919 Genes

To better assess the potential role of the two wild-type genes (designated as FTT0918 and FTT0919) in virulence, they were individually targeted for deletion from SCHU S4 using an allelic replacement method previously used to generate defined mutations in LVS. The method incorporated a counter-selection step to ensure that the antibiotic resistance genes as well as all other DNA present in the plasmid used to generate the crossover mutations were absent from the ensuing mutant strain. Deletion of one of the targeted genes, FTT0919, had no obvious effect on virulence. (However, because mice are highly sensitive to infection by *F. tularensis*, any subtle decrease in virulence caused by this mutation could be overlooked by this screening procedure. For instance, decreasing the virulence of SCHU S4 to that of a type B strain would not be detected in the murine model, since mice are highly susceptible to both subspecies whereas higher mammals such as rabbits, monkeys, and humans would be far less susceptible to the latter than the former.) Regardless, the ΔFTT0919 strain is clearly far more virulent than LVS or SCHU AV, and unlikely, therefore, to be acceptable as a vaccine candidate.

In contrast to the ΔFTT0919 strain, the ΔFTT0918 mutant showed significantly reduced virulence for mice. Moreover, mice that recovered from infection with this mutant were protected from subsequent challenge with a highly virulent type A strain. Despite its attenuation, ΔFTT0918 retained a greater residual virulence for mice than either LVS or SCHU AV. This is unsurprising since the latter two spontaneous mutants are missing additional genes some of which must encode additional virulence factors. By selectively deleting some of the latter genes from mutant ΔFTT0918 it should be possible to attenuate it to the same degree as SCHU AV to thereby produce a rationally attenuated strain with superior vaccine properties (safer and more effective) compared to LVS. Of course, the same technique used to generate mutant ΔFTT0918 can be used to delete additional genes from it.

ΔFTT0918 encodes for a 58-kDa protein with no close homology to any other known proteins. In its absence, strain ΔFTT0918 and LVS are rendered highly susceptible to in vitro killing by peroxynitrite. In an earlier examination of the host killing mechanisms of the LVS strain, it was observed that iNOS and to a minor degree phox, contributed to the bactericidal activity in vitro. However, on a molar basis, peroxynitrite was identified as a much more bactericidal molecule than nitric oxide or hydrogen peroxide. Thus, resistance to peroxynitrite may be an important factor for the virulence of wild-type *F. tularensis* strains. The fact that SCHU AV, which like LVS contains a defective FTT0918 gene, appears to be more resistant to this type of killing than ΔFTT0918 indicates that the mechanisms affecting the resistance are quite complicated. A simple explanation is that the hybrid gene product of the chimeric FTT0918 and FTT0919 gene that is expressed in SCHU AV has a residual function and explains the difference. However, since LVS also produces a similar hybrid protein but is susceptible to peroxynitrite-mediated killing it must be presumed that other strain-specific factors must also contribute to this phenomenon.

Effectiveness of ΔFTT0918 Mutant as Vaccine

Mice inoculated with the ΔFTT0918 mutant survived longer than those that were not inoculated, or those that were inoculated with the LVS mutant or a ΔiglC attenuated mutant, indicating that the ΔFTT0918 mutant has utility as a vaccine (Table 7). Further, the ΔFTT0918 mutant was disseminated to liver and spleen tissues more efficiently than the ΔiglC mutant (Table 2).

These results suggest that the ability to disseminate from sites of entry into the body to lymphoid tissues and to multiply intracellularly may be critical for priming of an effective, long-lasting protection, as evidenced by the marginal protection afforded by strain ΔiglC versus the other mutant strains of SCHU S4 examined herein.

EXAMPLES

Bacteria. *F. tularensis* LVS was originally obtained from the American Type Culture Collection. (ATCC 29684). The *F. tularensis* strain FSC033/snMF (subspecies *tularensis*) was originally isolated from a squirrel in Georgia USA, the strains SCHU S4 (subspecies *tularensis*), FSC237, and a spontaneous mutant of the SCHU S4 strain, SCHU AV (abbreviation for AVirulent) (also designated as FSC 043), were all obtained from the *Francisella* Strain Collection (FSC) of the Swedish Defence Research Agency, Umeå. The mutant strains ΔFTT0918, ΔFTT0919, and ΔiglC were all derived from the SCHU S4 strain as detailed below. For the present study, stock cultures of all strains were prepared by growing them as confluent lawns on cysteine heart agar supplemented with 1% (w/v) hemoglobin (CHAH). Bacteria were harvested after 48-72 h incubation at 37° C. in an atmosphere of 5% $CO_2$ into freezing medium consisting of modified Mueller Hinton broth containing 10% w/v sucrose. Stocks were aliquoted in a volume of 1 ml and stored at −80° C.

Construction of mutagenesis plasmids. Regions approximately 1,500-base pairs upstream and downstream of each targeted gene were amplified by PCR. The 5'-primers contained SalI restriction sites and the 3'-primers a BamHI site or a PstI site.

Each upstream fragment included the first 80 nucleotides and the downstream fragments the last 15 nucleotides of the respective gene. They were ligated to SalI/BamHI or SalI/PstI-digested plasmid pBlue-ScriptKS+ (Stratagene, La Jolla, Calif.). From the recombinant plasmids, the cloned DNA fragments were excised with SalI and BamHI and both fragments ligated simultaneously to SalI-digested pPV.

Conjugal transfer of plasmids. Early log cultures of $10^7$ CFU/ml of *E. coli* S17-1 carrying pPV-ΔFTT0918 or pPV-ΔFTT0919 or pPV-ΔiglC and $10^9$ CFU/ml of *F. tularensis* LVS were concentrated by centrifugation and resuspended in 50 µl of culture medium, mixed, and plated on either Luria agar (LA) or modified Gc-agar base plates. After incubation, cells were resuspended in PBS and plated on modified GC agar base plates containing 100 µg/ml of polymyxin B for counterselection of the donor *E. coli* strain (Golovliov, 2003) and 2.5 µg/ml of chloramphenicol. To select for a second recombination event, recombinant bacteria were plated on medium containing 5% sucrose. All sucrose-resistant colonies that were sensitive to chloramphenicol were selected for further analysis.

Exposure of *F. tularensis* to reactive molecular species in a cell-free system. Peroxynitrite (ONOO—) is generated from 3-morpholinosydnonimine hydrochloride (SIN-1) (Molecular Probes, Oregon, USA). Under physiological conditions, 1 mM SIN-1 generates 10 mM of ONOO—/min. *F. tularensis* bacteria were cultivated overnight and diluted to a density of approximately $2 \times 10^6$ bacteria/ml in PBS and to some tubes SIN-1 was added to a final concentration of 0.8 mM. The tubes were incubated at 37° C. and viable counts performed at 4 h.

Infection of Macrophages.

Peritoneal exudate cells (PEC) were obtained from mice three days after intraperitoneal injection of 2 ml of 10% proteose peptone. PEC were washed with DMEM (GIBCO BRL, Grand Islands, N.Y.) and resuspended at a density of $3 \times 10^6$ cells/ml in culture medium consisting of DMEM with 10% heat-inactivated fetal calf serum. The suspension was aliquotted in 100-µl volumes in 96-well tissue culture plates. After incubation for 2 h at 37° C., non-adherent cells were removed by washing and after an additional 24 h, *F. tularensis* bacteria were added to give a multiplicity of infection of 50 bacteria/PEC. The actual MOI was determined by retrospective plating, thus there were slight variations between experiments. After allowing uptake of bacteria to occur for 1.5 h, the macrophages were washed to remove extracellular bacteria. Macrophages were reconstituted in culture medium supplemented with 2 µg/ml of gentamicin to kill any remaining extracellular bacteria and incubated for indicated periods of time. Then, PEC were lysed with 0.1% dodeoxycholate and the number of intracellular bacteria determined by plating 10-fold serial dilutions.

Proteomic Analysis of Strains SCHU S4, SCHU AV and ΔFTT0918.

*Francisella* strains were plated for single colony growth on CHAH agar. At 72 h of incubation 200 colonies of one or other strain were resuspended in 12 times the estimated pellet volume of lysis solution (7 M urea, 2 M thiourea, 1% (w/v) DTT, 4% (w/v) CHAPS and 0.5% (w/v) ASB-14. Cell pellets were resuspended by vortexing, then were shaken for 30 minutes at room temperature and then incubated for at least four hours at 4° C. Unlysed cells and cell debris were removed by centrifugation at 14,000 g for 10 min. The supernatants were checked for sterility and stored at −20° C. until required. Protein concentrations of the extracts were determined using the RC-DC protein assay (Bio-Rad) or a modified Bradford Assay.

The extracted proteins were separated in the first dimension using either linear pH 4-7 gradient Ready Strips, 17 cm (Biorad, California, USA) or linear pH 6-11 gradient Immobiline drystrips, 18 cm (Amersham Biosciences, Uppsala, Sweden). In each case 100-300 µg of each protein solution was diluted in 350 µl of rehydration buffer (7 M urea, 2 M thiourea, 4% CHAPS, 0.5% ASB-14, 1% DTT, 1% v/v Pharmalyte pH 3-10 or pH 6-11, 0.003% Orange G). For ioselectric focusing in the basic pH range (pH 6-11) protein solutions were treated with Destreak Rehydration Solution (Amersham Biosciences) as per the manufacturer's instructions, prior to rehydration of the immobilized pH gradient strips (IPG). The samples were incubated for 1 hour with shaking, and then centrifuged at 10,000 g for 10 minutes. Proteins were loaded onto the IPG strips by in-gel rehydration overnight. Isoelectric focusing was conducted using a Protean IEF Cell (Bio-Rad). Proteins were focused at 200 V for 1 h, 500 V for 1 h, 5000 V for 5 h and then 5000 V for a total of 80 kVh. Next, IPG strips were equilibrated in 6 M urea, 50 mM Tris, pH 8.8, 30% w/v glycerol, 2% w/v SDS and 1 w/v % DTT for 20 minutes. The IPG strips were then equilibrated for another 20 minutes in the same solution containing 4% w/v iodoacetamide instead of DTT. Strips were then embedded on top of an SDS-PAGE gel (12% polyacrylamide; 190×190×1.5 mm gel)

using 0.5% w/v agarose 0.003% w/v bromophenol blue. Electrophoresis was then carried out using the Protean IIxi System with XL conversion kit (Bio-Rad) at 24 mA per gel for 5 hours. Following second dimension electrophoresis, gels were fixed for 1 hour in 10% v/v methanol, 7% v/v acetic acid, then stained overnight with Sypro Ruby (Bio-Rad). Background staining was removed by two 30 minute washes in 10% v/v methanol, 7% v/v acetic acid, prior to imaging with the Fluor-S MultiImager (Bio-Rad). The gels were then stained with silver nitrate, scanned and analyzed a second time.

Images of the scanned gels were made using PDQuest software (Bio-Rad). At least 4 replicate gel sets were run for each bacterial strain. Spot positions were matched between replicate gel sets and both matched and unmatched spots checked manually. Spots were considered absent if unmatched in all gel sets. Differential expression was considered greater than two-fold spot intensity difference after normalization of spot intensities. Protein spots consistently identified as being differentially expressed between strains were excised and cut into 1 mm cubes and placed in microcentrifuge tubes. Gel pieces were destained with 30 mM ferricyanide, 100 mM sodium thiosulphate for 5 minutes, and then washed three times with water. The gel pieces were dehydrated repeatedly with 100% acetonitrile, until the pieces blanched and became hard. Acetonitrile was then removed and gel pieces air-dried under a laminar flow hood. 20 µL of 20 ng/mL trypsin in 50 mM ammonium bicarbonate was then added to each tube and gel pieces incubated at 37° C. for 16 hours. Peptides were extracted from the gel pieces by sonication for 10 minutes.

The in-gel digests were analysed by nano-liquid chromatography-MS/MS using a 'CapLC' capillary chromatography system (Waters) coupled to a 'QTOF Ultima' hybrid quadrupole time-of-flight mass spectrometer (Waters). Peptide extracts were injected on a 75 µm internal diameter×150 mm PepMap $C_{18}$ nanocolumn (Dionex/LC packings) and resolved by gradient elution (5-75% acetonitrile, 0.12% formic acid in 30 minutes, 350 nl/min). MS/MS spectra were acquired on doubly, triply and quadruply charged ions. The experimentally collected MS/MS spectra were matched against the *Francisella* strain Schu 4 genome sequence using Mascot Daemon™. Results were evaluated according to the Mascot score, number of peptides identified and quality of MS/MS matching. A protein identification was considered positive if at least one peptide, with a Mascot score greater than 25 was matched.

Genomic characterization of strain SCHU AV. The chromosomal regions that contained the genes encoding the proteins altered or missing in strain SCHU AV were analyzed in detail by a combination of bioinformatic analysis of the published genome of the SCHU S4 strain and by PCR amplification and sequencing of the regions in strains SCHU AV and SCHU S4.

Administration of bacteria to mice. Specific-pathogen-free female BALB/c mice were purchased from Charles River Laboratories (St. Constant, Que.). Mice were maintained and used in accordance with the recommendations of the Canadian Council on Animal Care Guide to the Care and Use of Experimental Animals. Strain FSC 033 was found to be more virulent for mice than the SCHU S4 isolate used to generate the mutants of the present study since a 10 CFU intradermal (i.d.) challenge of the former kills mice 1-2 days earlier than the same challenge with the latter strain. Therefore, strain FSC033 was used as the wild-type challenge strain for all of the efficacy studies conducted herein. For aerosol exposure, thawed *F. tularensis* strain FSC033 was diluted in Mueller Hinton broth containing 20% (w/v) glycerol to a concentration of approximately $10^8$/CFU ml; for intradermal inoculations stocks were diluted in sterile saline. Actual concentrations of inocula were determined by plating 10-fold serial dilutions on CHAH.

Intradermal inocula (50 µl/mouse) were injected into the shaved mid-belly. Aerosols containing strain FSC033 were generated with a Lovelace™ nebuliser operating at a pressure of 40 p.s.i. to produce particles in the 4-6 µm range required for inhalation and retention in the alveoli. Mice were exposed to these aerosols for 7 min using a commercial nose-only exposure apparatus (In-tox Products, Albuquerque, N. Mex.). In each experiment, the generated aerosol was delivered to the exposure ports at a flow rate of 15 l/min, and at 80% relative humidity. This protocol results in the delivery of ~20 CFU to the lower airways of BALB/c mice. Aerosol exposures and i.d. challenges were performed in a federally-licensed small animal containment level 3 facility. Strain FSC033 was routinely lethal for naïve BALB/c mice following intradermal or aerosol challenge with 10 or fewer CFU. In the present study, mice were examined daily for signs of infection. Whenever feasible, mice were euthanized by $CO_2$ asphyxiation as soon as they displayed signs of irreversible morbidity. In our experience such mice were at most 24 hours from death, and time to death of these animals was estimated on this premise.

A spontaneous mutant, SCHU AV of strain SCHU S4 is attenuated in vitro and in vivo but affords effective protection against challenge with virulent type A strain, FSC033. Screening of the *Francisella* Strain Collection (FSC) revealed an attenuated strain, FSC043, derived from the prototypic subspecies *tularensis* strain, SCHU S4. This strain, henceforth designated SCHU AV (avirulent), was found to be markedly attenuated for multiplication in PEC (Table 1) and J774 cells. In fact, a rapid decline was observed within 6 h of exposure to these macrophage populations, but thereafter some intracellular multiplication occurred up to 12 h. Eradication occurred within 24 h. In contrast, the number of intracellular SCHU S4 bacteria increased 2 $log_{10}$ within 12 h. Thereafter, a decline was seen. However, during this phase of the infection with virulent but not attenuated *F. tularensis*, a cytopathogenic effect was observed morphologically. Thus, the rapid intracellular multiplication of the strain confers a rapid cytopathogenic effect and most likely, this explains the decrease in intracellular numbers of virulent bacteria after 12 h.

In several separate experiments BALB/c mice were challenged intradermally with $10^2$-$10^8$ CFU of SCHU AV or LVS. All LVS challenged BALB/c mice displayed overt signs of illness between days 4-11 (hunched gait, pilo-erection, lethargy) and some mice inoculated with $10^7$ or $10^8$ CFU died by day 8 of infection. No other mice died during the next 28 days. In contrast, only mice challenged with >$10^6$ CFU of SCHU AV displayed such signs of infection and no mice inoculated with this strain died at any test dose.

To further examine the relative virulence of LVS and SCHU AV, BALB/c mice were intradermally challenged with $10^6$ CFU of one or other strain, killed on day 4 of infection and bacterial burdens in the skin, liver, and spleen determined (Table 2). By this time, LVS was present at higher levels than SCHU AV in the skin, liver, and spleen. Moreover, large macroscopic skin lesions were visible at the site of inoculation of LVS, but not SCHU AV by this time (FIG. 1). Similarly, when inoculated intravenously, SCHU AV grew less than virulent type A or B strains or LVS in the livers, spleens, and lungs of mice (Table 3).

BALB/c mice were intradermally inoculated with $10^6$ CFU of LVS or SCHU AV. The former mice showed overt signs of disease between days 3-6 of infection whereas the latter mice remained healthy. All immunized mice survived and were challenged 77 days later intradermally or by aerosol with subsp. *tularensis* strain FSC 033 (Table 4). It has been shown that immunization of BALB/c mice with LVS leads to excellent protection against intradermal challenge but only weak protection against low dose aerosol challenge (see also Table 4). The SCHU AV immunization afforded as good protection as LVS against intradermal challenge and better protection against aerosol challenge.

Groups of mice (n=3) were challenged intradermally with 150 CFU of strain FSC033 120 days after immunization with LVS or SCHU AV. Mice were killed on day 3 of infection and *Francisella* burdens in livers, spleens, and lungs determined (Table 5). Numbers in parentheses show the proportion of organs infected. Again, this study showed that SCHU AV immunization was at least as effective as LVS immunization at controlling disseminated infection with a type A strain.

Proteomic Analysis of Strain SCHU AV.

Figure 2:
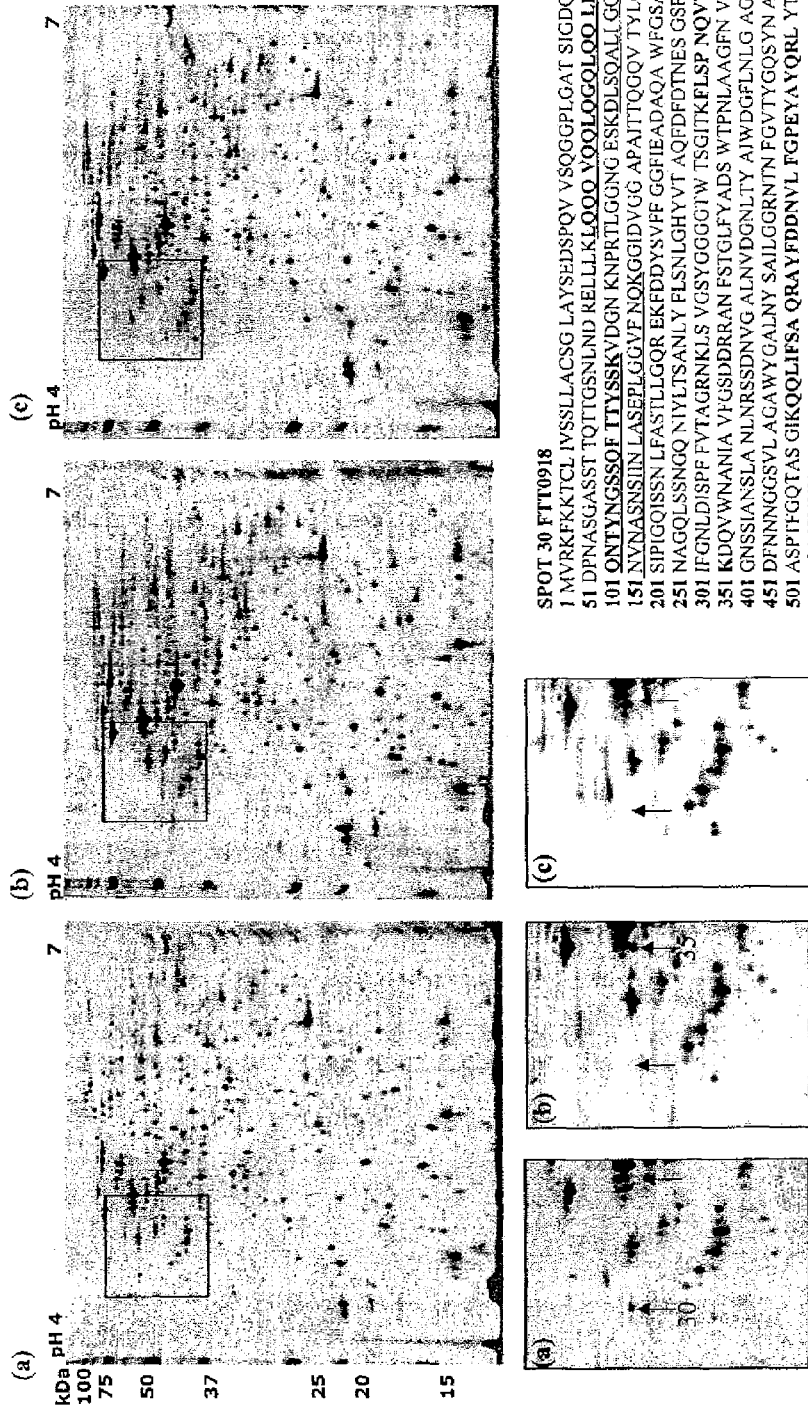
FIG. 2 illustrates proteomic comparisons of *F. tularensis* strains. X 2D-PAGE of *Francisella tularensis* strains (a) SCHU S4, (b) SCHU AV and (c) mutant ΔprpA visualized by staining with sypro ruby. Replicate gels within experimental groups were compared. Boxed regions in large gels correspond to enlarged areas below. Protein sequences for FTT0918 (spot 30; SEQ ID NO.: 2) and FTT0919 (spot 35; SEQ ID NO.: 3) are shown on the bottom right. Amino acid sequences underlined correspond to those peptides detected by LC-MSMS of a tryptic digest of spot 35 from SCHU AV, whilst those in bold are those detected from a tryptic digest of spot 30.

Two-dimensional gel electrophoresis (2D-PAGE) was used to compare the proteomes of the virulent SCHU S4, and attenuated SCHU AV. Protein spots that exhibited an intensity difference of at least two-fold between strains were excised and identified by mass spectrometric analysis of their in-gel tryptic digests. Gels in the pH ranges 4-7 and 6-11 were run. The majority of the protein spots resolved in the pH range 4-7, and within this range a total 10 spots were identified in SCHU AV as differing in abundance or absent when compared to the virulent SCHU S4. Six spots were undetectable and three were decreased in abundance in comparison to SCHU S4. The putative identities of these proteins are shown in Table 6. In contrast, one spot (35) was observed only in SCHU AV (FIG. 2). The protein spot was found to contain peptides corresponding to two proteins, FTT0918 and FTT 0919, found in the parental strain. Both are identified as hypothetical proteins with no known homology to other proteins and no assigned function. FTT0918 was also identified as spot 30 in the parental strain (FIG. 2). MS analysis for spot 30 showed a good peptide coverage throughout the protein sequence (FIG. 2). In contrast, MS analysis of SCHU AV spot 35 identified peptides confined to the first half of FTT0919 amino acid sequence and the second half of FTT0918 amino acid sequence. The genes corresponding to these two proteins are in close proximity on the chromosome; FTT0918 is coded from 927667-929340 b.p. and FTT0919 from 9292357-930802 b.p. Thus, it appears that a deletion mutation overlapping these genes resulted in the creation of a novel gene coding for a hybrid protein corresponding to the N terminus of FTT0918 and the C terminus of FTT019. We have found evidence for the presence of a similar hybrid protein in LVS, and the hybrid gene for this protein is reported in the current LVS genome sequence database.

Characteristics of defined mutants of strain SCHU S4. The two genes found to be partially missing in both strains LVS and SCHU AV were subjected to the deletion strategy using plasmid pPV and both mutants were obtained in strain SCHU S4. Additionally, the ΔiglC gene that when deleted from LVS resulted in its further attenuation to complete avirulence for mice was deleted from SCHU S4.

Defined mutant ΔFTT0919 missing the gene coding for protein FTT0919 remained highly virulent for mice by the i.d. route (i.e. $LD_{50}$<50 CFU), and so was not further evaluated as a live vaccine candidate. In contrast, mutant ΔFTT0918 missing the gene encoding for protein FTT0918 was highly attenuated compared to the parental strain (i.d. $LD_{50}$ ~$10^5$ CFU versus <10 CFU respectively based on accumulated data from 4 separate experiments). Proteomic analysis confirmed that it lacked the expected protein spot 30 in SCHU S4 (FIG. 2). When inoculated intradermally at a dose of 100 CFU, mutant ΔFTT0918 multiplied less than the parental strain and caused a much less overt tissue reaction at this site, and disseminated less to internal organs (Table 2; FIG. 1). Indeed, at this test dose, it appeared as attenuated as LVS (Table 2), though the lower $LD_{50}$ of the former strain indicated it was more virulent than the latter or SCHU AV at higher doses. Likewise the fact that mutant ΔFTT0918 persisted and multiplied in PEC whereas SCHU AV was killed by these host cells suggests that the former is more virulent than the latter (Table 1). At the opposite end of the spectrum from mutant ΔFTT0919, mutant ΔiglC appears to be totally avirulent in that it failed to induce any overt disease in mice even at an i.d. dose of $10^8$ CFU. Interestingly, this mutant persisted at least as well as SCHU AV in the skin, but appeared less able to disseminate to internal organs (Table 2). Mice immunized intradermally with defined mutants of *F. tularensis* were challenged 8-9 weeks later with virulent strain FSC033 by the intradermal or aerosol route respectively and their survival monitored (Table 7). Mutant ΔFTT0918 was at least as effective a live vaccine as LVS in these studies at combating a systemic challenge with virulent type A *F. tularensis* whereas mutant ΔiglC performed poorly. The fact a ΔiglC mutant of SCHU S4 was unable to act as a protective vaccine despite being severely attenuated and persisting at the site of inoculation in the skin demonstrates that attenuation per se is not a sufficient criterion by which to determine utility. Against an aerosol challenge, all mice immunized with mutant ΔFTT0918 survived longer than any of those immunized with LVS.

In vitro, mutant ΔFTT0918 was better able to survive and replicate in PEC than SCHU AV (Table 1). However, it was much more susceptible than the latter to peroxynitrite-mediated killing (Table 8).

It is understood that the examples described above in no way serve to limit the true scope of this invention, but rather are presented for illustrative purposes.

REFERENCES

Inclusion of a reference is neither an admission nor a suggestion that it is relevant to the patentability of anything disclosed herein Sjostedt A. Virulence determinants and protective antigens of *Francisella tularensis*. Curr Opin Microbiol 2003; 6: 66-71.

Eigelsbach H T, Downs C. Prophylactic effectiveness of live and killed tularemia vaccines. I. Production of vaccine and evaluation in the white mouse and guinea pig. J Immunol 1961; 87:415-25.

Saslaw S, Eigelsbach H T, Prior J A, Wilson H E, Carhart S. Tularemia vaccine study II. Respiratory challenge. Arch Int Med 1961; 107: 702-14.

Saslaw S, Eigelsbach H T, Wilson H E, Prior J A, Carhart S. Tularemia vaccine study. I. Intracutaneous challenge. Arch Int Med 1961; 107: 689-701.

Burke D S. Immunization against tularemia: Analysis of the effectiveness of live *Francisella tularensis* vaccine in prevention of laboratory-acquired tularemia. J Infect Dis 1977; 135:55-60.

Conlan J W. 2004. Vaccines against *Francisella tularensis*—past, present and future. Expert Review of Vaccines. 3: 307-314.

Eigelsbach H T, Tulis J, Overholt E L, Griffith W R. Aerogenic immunization of the monkey and guinea pig with live tularemia vaccine. Proc. Soc Exptl Biol Med 1961; 108: 732-34.

Hornick R B, Eigelsbach H T. Aerogenic immunization of man with live tularemia vaccine. Bact Revs 1966; 30:532-38.

Conlan J W, Shen H, KuoLee R, Zhao X, and Chen W. 2005. Aerosol-, but not intradermal-immunization with the live vaccine strain of Francisella tularensis protects mice against subsequent aerosol challenge with a highly virulent type A strain of the pathogen by an αβ T cell- and interferon gamma-dependent mechanism. Vaccine 2005; 23: 2477-2485.

Johansson A, Ibrahim A, Goransson I, Eriksson U, Gurycova D, Clarridge J E, Sjostedt A. Evaluation of PCR-based methods for discrimination of Francisella species and subspecies and development of a specific PCR that distinguishes the two major subspecies of Francisella tularensis. J Clin Micro 2000; 38: 4180-85.

Golovliov I, Sjostedt A, Mokrievich A, Pavlov V. A method for allelic replacement in Francisella tularensis. FEMS Microbiol Lett 2003; 222: 273-280.

Conlan J W, Chen W, Shen H, Webb A, KuoLee R. Experimental tularemia in mice challenged by aerosol or intradermally with virulent strains of Francisella tularensis: Bacteriologic and histopathological studies. Microb Pathog 2003; 34: 239-48.

Golovliov, I., Ericsson, M., Sandstrom, G., Tärnvik, A., and Sjöstedt, A. Identification of proteins of Francisella tularensis induced during growth in macrophages and cloning of the gene encoding a prominently induced 23-kilodalton protein. Infect Immun 1997; 65, 2183-2189.

Lai X, Golovliov I, Sjostedt A. Expression of IgIC is necessary for intracellular growth and induction of apoptosis in murine macrophages by Francisella tularensis. Microbial Pathogenesis 2004; 37: 225-30.

Lindgren H, Golovliov I, Baranov V, Ernst R K, Telepnev M, Sjostedt A. Factors affecting the escape of Francisella tularensis from the phagolysosome. J Med Micro 2004; 53: 1-6.

Lauriano C M, Barker J R, Yoon S-S, Nano F E, Arulanandam B P, Hassett D J, Klose K E. MgIA regulates transcription of virulence factors necessary for Francisella tularensis intraamoebae and intramacrophage survival. PNAS 2004; 101: 4246-4249.

TABLE 1

Viable counts in PEC infected with the indicated *F. tularensis* strain[a].

| Bacterial strain[a] | No. of bacteria (log$_{10}$ ± SD)[b] | | | |
|---|---|---|---|---|
| | 0 h | 6 h | 12 h | 24 h |
| SCHU S4 | 2.5 | 2.4 | 4.6 | 3.1 |
| FSC043/SCHU AV | 2.4 | 0.8* | 1.9* | <0.5* |
| ΔFTT0918 | 2.7 | 2.6 | 3.6 | 3.3 |

[a]The indicated *F. tularensis* strain was allowed to infect the cells at MOI 100.
[b]Data represent the mean log$_{10}$ CFU ± SD of 3 cultures.
*Indicates that the CFU is significantly higher (p < 0.05, Wilcoxon asymptotic test) than the value at 0 h.

TABLE 2

Growth of *F. tularensis* strains in host tissues following intradermal inoculation of the pathogen.

| F. tularensis strain | Intradermal inoculum | Log$_{10}$ ± SD CFU of *Francisella* in tissues on day 4 of infection (n = 3)[a] | | |
|---|---|---|---|---|
| | | skin | liver | spleen |
| SCHU AV | 10$^6$ CFU | 4.00 ± 0.48 | 3.81 ± 0.08 | 4.57 ± 0.09 |
| LVS | 10$^6$ CFU | 6.28 ± 0.21 | 5.76 ± 0.50 | 5.88 ± 0.47 |
| ΔiglC mutant | 10$^6$ CFU | 5.31 ± 0.43 | 2.30 (1/3)[b] | 3.09 ± 0.69 |
| SCHU S4 | 10$^2$ CFU | 7.37 ± 0.40 | 7.09 ± 0.83 | 7.77 ± 0.91 |
| LVS | 10$^2$ CFU | 6.65 ± 0.58 | 3.65 ± 1.10 | 4.37 (2/3)[c] |
| ΔFTT0918 mutant | 10$^2$ CFU | 5.66 ± 0.73 | 3.50 ± 0.29 | 4.36 ± 1.33 |

[a]In separate experiments, mice were inoculated intradermally with either 10$^6$ or 10$^2$ CFU of the stated F. tularensis strain. Mice were killed on day 4 of infection and bacterial burdens determined.
[b]Bacteria only detected in 1/3 organs;
[c]Bacteria only detected in 2/3 organs (lower detection limit = 200 CFU/organ).

TABLE 3

Growth of *F. tularensis* strains in host tissues following intravenous inoculation of the pathogen.

| F. tularensis strain | Log$_{10}$ ± SD CFU *F. tularensis*/organ (n = 3) | | | |
|---|---|---|---|---|
| | lung | liver | spleen | blood* |
| FSC033 (type A) | >8.0 | >9.0 | >9.0 | >8.0 |
| FSC108 (type B) | 3.97 ± 0.34 | 7.26 ± 0.32 | 7.35 ± 0.20 | 3.58 ± 0.77 |
| LVS (attenuated type B) | 2.31 ± 1.02 | 5.03 ± 0.12 | 5.18 ± 0.12 | <2.00 (0/3) |
| SCHU AV (attenuated type A) | <1.3 (0/3) | <2.3 (2/3) | 3.16 ± 0.66 | <2.00 (0/3) |

[a]Approximately 100 CFU of the indicated strains of *F. tularensis* were intravenously inoculated into BALB/c mice (n = 3 per group), and bacterial burdens in organs on day 3 of infection were determined.
[b]CFU/ml of blood. Numbers in parentheses indicate proportion of organs infected.

TABLE 4

Protective immunity against strain FSC033 (type A; subsp. *tularensis*) elicited by intradermal immunization with LVS or SCHU AV[a].

| Immunizing strain | Challenge route and dose | Individual times to death (days) | Median time to death (days) |
|---|---|---|---|
| None | i.d. 10 CFU | 5, 5, 6, 6, 6 | 6 |
| LVS | i.d. 1000 CFU | 5, >35, >35, >35, >35 | >35 |

TABLE 4-continued

Protective immunity against strain FSC033 (type A; subsp. *tularensis*) elicited by intradermal immunization with LVS or SCHU AV[a].

| Immunizing strain | Challenge route and dose | Individual times to death (days) | Median time to death (days) |
|---|---|---|---|
| SCHU AV | i.d. 1000 CFU | 11, 12, >35, >35, >35 | >35 |
| None | aerosol ~10 CFU | 5, 5, 5, 5, 6 | 5 |
| LVS | aerosol ~10 CFU | 6, 6, 11, 13, >35 | 11 |
| SCHU AV | aerosol ~10 CFU | 5, 7, >35, >35, >35 | >35 |

[a]Mice immunized 77 days earlier by id inoculation with $10^6$ CFU LVS or SCHU AV and age-matched controls were challenged intradermally or by aerosol with various doses of virulent type A *F. tularensis* strain 33, and survival monitored.

TABLE 5

Growth of virulent strain FSC033 in organs of control mice and mice vaccinated with LVS or SCHU AV[a].

| Immunizing strain | *Francisella* burden on day 3 of infection (mean $\log_{10}$ ± SD) | | |
|---|---|---|---|
| | Lungs | liver | Spleen |
| None | 5.18 ± 2.03 | 7.49 ± 0.86 | 8.33 ± 1.13 |
| LVS | <1.30 (0/3) | 2.91 ± 0.41 | 3.62 ± 0.25 |
| SCHU AV | <1.3 (0/3) | <2.25 (1/3) | 2.63 ± 1.74 |

[a]mice (n = 3/group) immunized 120 days earlier with $10^6$ CFU of LVS or SCHU AV were challenged intradermally 120 days later with 150 CFU of *F. tularensis* type A strain FSC033. Mice were killed on day 3 of infection and *Francisella* burdens in livers, spleens, and lungs determined.
Numbers in parentheses show the proportion of organs infected.

TABLE 6

Differentially expressed proteins

| Spot No.[a] (FTT No.)[b] | MW, pI Theoretical[c] | Observed MW, pI[d] | Mascot Score[e] | Sequence Coverage[f] | Protein Name[g] | Protein i.d.[h] |
|---|---|---|---|---|---|---|
| Protein Spots Not Observed in SCHU AV | | | | | | |
| 2 (1355) | 22.1, 6.77 | 18.2, 6.05 | 132 | 20 | Conserved hypothetical protein | YP_170307.1 |
| 6 (0049/0192) | 55.1, 4.49 | 61.4, 4.85 | 774 | 41 | N utilization substance protein A | YP_169124.1 |
| | 66.2, 5.55 | 61.4, 4.85 | 60 | 3 | Lysyl-tRNA synthetase | YP_169253.1 |
| 22 (0655) | 26.8, 4.68 | 34.9, 4.70 | 450 | 41 | Hypothetical protein | YP_169673.1 |
| 28 (0409) | 49.6, 5.77 | 50.0, 6.16 | 108 | 18 | Glycine cleavage system P protein, subunit 1 | YP_169454.1 |
| 30 (0918) | 58.7, 4.75 | 56.6, 4.45 | 263 | 14 | Hypothetical protein | YP_169915.1 |
| 31 (0007/1129c) | 66.9, 5.49 | 67.0, 5.85 | 826 | 42 | Aspartyl-tRNA synthetase | YP_169088.1 |
| | 63.0, 5.46 | 67.0, 5.85 | 493 | 35 | Cyanophycin synthetase | YP_170102.1 |
| Protein Spots with decreased abundance in SCHU AV | | | | | | |
| 19 (0721c) | 82.4, 5.37 | 83.0, 5.61 | 709 | 35 | Peroxidase/catalase | YP_169735.1 |
| 21 (0223c) | 25.8, 5.36 | 26.2, 5.72 | 202 | 27 | Lactam utilization protein | YP_169278.1 |
| 29 (0036/0438) | 46.2, 5.61 | 47.5, 5.99 | 431 | 27 | NADH dehydrogenase I, F subunit | YP_169112.1 |
| | 51.5, 5.58 | 47.5, 5.99 | 167 | 10 | UDP-N-acetylmuramate: L-alanyl-gamma-D-glutamyl-meso-diaminopimelate ligase | YP_169478.1 |
| Protein Spots Uniquely expressed in SCHU AV | | | | | | |
| 35 (0918/0919) | 58.7, 4.75 | 55.0, 5.02 | 211 | 11 | Hypothetical protein | YP_169915.1 |
| | 52.8, 5.16 | 55.0, 5.02 | 252 | 14 | Hypothetical protein | YP_169916.1 |

Proteins were identified by LC-MS/MS. Mascot (Matrix Science, London, UK) was then used to match the MS/MS spectra against the translated *Francisella* genome sequence (Refseq: NC_006570). Proteins listed are those that were observed to be differentially expressed when comparing the proteome maps of strains SCHU S4 and SCHU AV.
[a]Number used to annotate spot on 2DE proteome maps
[b]*Francisella* genome locus tag (FTTxxxx)
[c]Theoretical molecular mass (kDa) and pI, calculated from the amino acid sequence of the translated open reading frame
[d]Experimental molecular mass (kDa) and pI, estimated using PDQuest software
[e]Total Mascot Score for peptides identified. A score of >30 was required for positive identification each individual polypeptide
[f]Sequence coverage, based on the peptides identified
[g]Name of identified protein, based upon *Francisella* genome sequence
[h]Accession number according to the NCBI

TABLE 7

Protective immunity against strain FSC033 (type A; subsp. *tularensis*) elicited by intradermal immunization with LVS or defined mutants of SCHU S4.

| Immunizing strain (dose) | Challenge route and dose | Individual times to death (days) | Median time to death (days) |
|---|---|---|---|
| None | i.d. 10 CFU | 4, 4, 5, 5, 5 | 5 |
| LVS ($10^6$) | i.d. 500 CFU | >35, >35, >35, >35, >35 | >35 |
| ΔFTT0918 mutant ($10^{5-6}$) | i.d. 500 CFU | >35, >35, >35, >35, >35 | >35 |
| ΔiglC mutant ($10^6$) | i.d. 500 CFU | 4, 7, 7, 7, 8 | 7 |
| None | aerosol ~10 CFU | 4, 5, 5, 5, 5 | 5 |
| LVS ($10^7$) | aerosol ~10 CFU | 5, 7, 7, 7 | 7 |
| ΔFTT0918 mutant ($10^{5-6}$) | aerosol ~10 CFU | 9, 11, 11, 19, >30, >30 | 15 |
| ΔiglC mutant ($10^7$) | aerosol ~10 CFU | 5, 5, 6, 6, 6 | 6 |

[a]Mice (n = 4-6) immunized by intradermal inoculation with the indicated strain and age-matched control mice were challenged intradermally 8 weeks later with ~500 CFU of type A strain FSC033, or by aerosol 9 weeks later with ~10 CFU of FSC033 and survival monitored.

TABLE 8

Survival of *F. tularensis* strains in PBS when exposed to SIN-1.

| Bacterial strain | SIN-1 | No. of bacteria ($\log_{10}$ CFU)[a] 0 h | 4 h |
|---|---|---|---|
| SCHU S4 | − | 6.9 | 7.0 |
| SCHU S4 | + | 6.9 | 6.6 |
| FSC043 | − | 6.9 | 6.9 |
| FSC043 | + | 6.9 | 6.3 |
| ΔFTT0918 | − | 6.7 | 6.4 |
| ΔFTT0918 | + | 6.7 | 4.1* |

[a]*F. tularensis* bacteria were exposed to SIN-1 (0.8 mM) for 4 h at 37° C. Thereafter, viable counts were determined by plating of bacteria.
*indicates that P < 0.05 according to Wilcoxon's non-parametric test when compared to SIN-1-treated SCHU S□ bacteria.

TABLE 9

Nucleotide sequence of FTT0918(SEQ ID NO.: 1)

The gene sequence has been deposited as part of the complete genome of *Francisella tularensis* strain SCHU S4 (accession number AJ749949). The deduced protein has the identification CAG45551.1.

Number of nucleotides: 1674

Number of putative encoded amino acids: 557

Molecular weight: 58713.5

The following information is contained in GenBank:
Position: 927667 . . . 929340

/locus_tag = "FTT0918"

/note = "ORF ftt0918"

/codon_start = 1

/transl_table = 11

TABLE 9-continued

Nucleotide sequence of FTT0918(SEQ ID NO.: 1)

/product = "hypothetical protein"

/protein_id = "CAG45551.1"

/db_xref = "GI: 56604511"

/db_xref = "UniProt/TrEMBL: Q5NGC7"

GTGGTGCGTAAATTTAAAAAAACCTGTTTGATAGTTAGTAGTTTATTGGC

TTGTAGTGGTTTAGCTTATTCTGAAGATTCTCCTCAAGTTGTTTCACAAG

GGGGGCCTCTTGGAGCTACTAGTATTGGTGATCAAAACCTTGGACAGCCA

GATCCAAATGCTAGTGGAGCCTCTTCAACAACACAGACTACCGGTTCAAA

TCTAAATGATAGGGAACTTTTGCTAAAATTACAGCAGCAGGTACAGCAAC

TTCAGGGACAATTACAACAGCTAAAAGCACAGGGTAATGGTGGTGGATTA

CAGAATACCTATAATGGTAGTTCGCAGTTTACTACTTACAGCTCAAAAGT

TGATGGTAATAAAAATCCTCGTACGCTTGGAGGCAATGGTGAGAGTAAAG

ATCTGAGTCAGGCTTTGATTGGTGGTCAAACGTCGTCAGATATTATGGGG

AATGTTAATGCTAGTAACTCTATCATTAATTTAGCTTCTGAGCCATTAGG

AGGCGTCTTTAACCAAAAAGGCGGTATCGACGTTGGTGGAGCTCCGGCGA

TTACAACACAAGGTCAAGTTACCTACTTAGGTTCGTACTCTGGTAACAAC

AGTATTCCAATTGGTCAGATTTCTTCTAACCTTTTTGCTTCTACATTGTT

GGGTCAAAGAGAGAAGTTTGATGACTACTCTGTATTCTTTGGTGGCTTTA

TAGAAGCAGATGCCCAAGCTTGGTTTGGTAGTGCTGTTACTAAGGTGCAA

AATGCTGGCCAGTTATCTAGCAATGGCCAAAATATATATTTAACATCAGC

TAATTTATATTTCTTATCAAATCTTGGTCATTATGTAACAGCTCAGTTTG

ATTTTGATACTAATGAGTCAGGAAGTTTTAGTTTAGGTAATGCTTTTGTA

ATTTTTGGTAACTTAGATATATCACCATTCTTCGTAACAGCAGGTAGAAA

CAAGCTATCTGTTGGCTCATATGGTGGTGGTGGTACTTGGACTAGCGGTA

TCACCAAATTTCTATCACCAAATCAGGTTACTAACGTATCTATTGACTAT

AAAGATCAAGTCTGGAACGCCAACATTGCAGTATTTGGCTCTGATGATAG

ACGTGCAAACTTCTCAACAGGTTTATTCTATGCTGATAGCTGGACACCAA

ACTTAGCGGCTGGTTTTAACGTAGGTTATGTCTTTAATATTGCTGGTGCT

GGTAACTCTTCGATTGCTAACTCATTAGCTAACTTAAATCGTAGTAGTGA

TAATGTGGGAGCTTTAAACGTTGACGGCAACTTAACTTATGCAATTTGGG

ATGGATTTTTAAACTTAGGAGCAGGTTGGGCTAGTACTACGACAAAAGAA

GATTTTAATAATAATGGTGGTAGTGTACTTGCTGGGGCATGGTATGGAGC

ACTTAACTATTCTGCGATACTTGGTGGTAGAAATACTAACTTCGGTGTGA

CTTATGGTCAATCATATAATGCTGCAGCTATCCCAATGGAGACAGCAAAT

GCTTCACCAACTTTCGGTCAAACAGCATCTGGTATCAAACAGCAACTTAT

CTTCTCGGCTCAGCGAGCTTACTTTGATGACAATGTTCTATTTGGTCCTG

AATATGCGTATCAAAGACTATATACTGGCGAACATATGAATACAATTACT

CTGGATATGTCGGTATACGTATAA

TABLE 9-continued

Nucleotide sequence of FTT0918(SEQ ID NO.: 1)

Putative amino acid sequence: (SEQ ID. NO.: 2)
MVRKFKKTCLIVSSLLACSGLAYSEDSPQVVSQGGPLGATSIGDQNLGQP
DPNASGASSTTQTTGSNLNDRELLLKLQQQVQQLQGQLQQLKAQGNGGGL
QNTYNGSSQFTTYSSKVDGNKNPRTLGGNGESKDLSQALIGGQTSSDIMG
NVNASNSIINLASEPLGGVFNQKGGIDVGGAPAITTQGQVTYLGSYSGNN
SIPIGQISSNLFASTLLGQREKFDDYSVFFGGFIEADAQAWFGSAVTKVQ
NAGQLSSNGQNIYLTSANLYFLSNLGHYVTAQFDFDTNESGSFSLGNAFV

TABLE 9-continued

Nucleotide sequence of FTT0918(SEQ ID NO.: 1)

IFGNLDISPFFVTAGRNKLSVGSYGGGGTWTSGITKFLSPNQVTNVSIDY
KDQVWNANIAVFGSDDRRANFSTGLFYADSWTPNLAAGFNVGYVFNIAGA
GNSSIANSLANLNRSSDNVGALNVDGNLTYAIWDGFLNLGAGWASTTTKE
DFNNNGGSVLAGAWYGALNYSAILGGRNTNFGVTYGQSYNAAAIPMETAN
ASPTFGQTASGIKQQLIFSAQRAYFDDNVLFGPEYAYQRLYTGEHMNTIT
LDMSVYV

---

We claim:

1. An isolated mutant of *Francisella tularensis* wherein the nucleotide sequence that encodes an amino acid sequence comprising SEQ ID NO:2 in wild-type *Francisella tularensis* is deleted, resulting in a lack of functional prpA and attenuated virulence.

2. The isolated mutant of claim 1, wherein the mutant *Francisella tularensis* is a mutant SCHU S4 strain of *Francisella tularensis*.

3. The isolated mutant of claim 1, further comprising the deletion of one or more than one gene other than the nucleotide sequence that encodes amino acid SEQ ID NO:2, resulting in a rationally attenuated combined gene deletion mutant.

4. A composition comprising the mutant of claim 1 and a pharmaceutically acceptable diluent, carrier, vehicle or excipient.

5. The composition of claim 4, for the immunization of a human or other mammal against virulent strains of *F. tularensis*.

6. The composition of claim 4, wherein the mutant is alive.

7. The composition of claim 4, for the immunization of a human or other mammal against intradermal challenge by virulent strains of *F. tularensis*.

8. The composition of claim 4, for the immunization of a human or other mammal against aerosol challenge by virulent strains of *F. tularensis*.

9. A method of reducing the susceptibility of humans or other mammals to infection by virulent strains of *F. tularensis* comprising the step of exposing a human or other mammal to a sufficient amount of the composition of claim 5 so as to reduce the susceptibility of the human or other mammal to infection by virulent *F. tularensis*.

10. A method of producing a mutant as claimed in claim 1, comprising the steps of:
    a) obtaining cells of a virulent *F. tularensis* strain;
    b) deleting the nucleotide sequence that encodes an amino acid sequence comprising SEQ ID NO:2;
    c) selecting for viable cells with attenuated virulence and deletion of the nucleotide sequence that encodes an amino acid sequence comprising SEQ ID NO:2; and
    d) isolating said cells with attenuated virulence and deletion of the nucleotide sequence that encodes an amino acid sequence comprising SEQ ID NO:2.

11. The method of claim 10, wherein the virulent *F. tularensis* strain is SCHU S4.

12. The mutant as claimed in claim 1, wherein the nucleotide sequence comprises SEQ ID NO:1.

13. The mutant as claimed in claim 1, wherein the mutant is that of deposit accession number CCUG 59671.

14. The method as claimed in claim 10, wherein the nucleotide sequence comprises SEQ ID NO:1.

* * * * *

SEQUENCE LISTING

<160> NUMBER OF SEQ ID NOS: 3

<210> SEQ ID NO 1
<211> LENGTH: 1674
<212> TYPE: DNA
<213> ORGANISM: Francisella tularensis

<400> SEQUENCE: 1

```
gtggtgcgta aatttaaaaa aacctgtttg atagttagta gtttattggc ttgtagtggt      60
ttagcttatt ctgaagattc tcctcaagtt gtttcacaag gggggcctct tggagctact     120
agtattggtg atcaaaacct tggacagcca gatccaaatg ctagtggagc ctcttcaaca     180
acacagacta ccggttcaaa tctaaatgat agggaacttt tgctaaaatt acagcagcag     240
gtacagcaac ttcagggaca attacaacag ctaaaagcac agggtaatgg tggtggatta     300
cagaatacct ataatggtag ttcgcagttt actacttaca gctcaaaagt tgatggtaat     360
aaaaatcctc gtacgcttgg aggcaatggt gagagtaaag atctgagtca ggcttttgatt    420
ggtggtcaaa cgtcgtcaga tattatgggg aatgttaatg ctagtaactc tatcattaat     480
ttagcttctg agccattagg aggcgtcttt aaccaaaaag gcggtatcga cgttggtgga     540
gctccggcga ttacaacaca aggtcaagtt acctacttag gttcgtactc tggtaacaac     600
agtattccaa ttggtcagat ttcttctaac cttttttgctt ctacattgtt gggtcaaaga     660
gagaagtttg atgactactc tgtattcttt ggtggcttta tagaagcaga tgcccaagct     720
tggtttggta gtgctgttac taaggtgcaa atgctggcc agttatctag caatggccaa      780
aatatatatt taacatcagc taatttatat ttcttatcaa atcttggtca ttatgtaaca     840
gctcagtttg attttgatac taatgagtca ggaagtttta gtttaggtaa tgcttttgta     900
atttttggta acttagatat atcaccattc ttcgtaacag caggtagaaa caagctatct     960
gttggctcat atggtggtgg tggtacttgg actagcggta tcaccaaatt tctatcacca    1020
aatcaggtta ctaacgtatc tattgactat aaagatcaag tctggaacgc aacattgca     1080
gtatttggct ctgatgatag acgtgcaaac ttctcaacag gtttattcta tgctgatagc    1140
tggacaccaa acttagcggc tggttttaac gtaggttatg tctttaatat tgctggtgct    1200
ggtaactctt cgattgctaa ctcattagct aacttaaatc gtagtagtga taatgtggga    1260
gctttaaacg ttgacggcaa cttaacttat gcaatttggg atggattttt aaacttagga    1320
gcaggttggg ctagtactac gacaaaagaa gatttttaata ataatggtgg tagtgtactt    1380
gctggggcat ggtatggagc acttaactat tctgcgatac ttggtggtag aaatactaac    1440
```

-continued

```
ttcggtgtga cttatggtca atcatataat gctgcagcta tcccaatgga gacagcaaat   1500
gcttcaccaa ctttcggtca aacagcatct ggtatcaaac agcaacttat cttctcggct   1560
cagcgagctt actttgatga caatgttcta tttggtcctg aatatgcgta tcaaagacta   1620
tatactggcg aacatatgaa tacaattact ctggatatgt cggtatacgt ataa         1674
```

<210> SEQ ID NO 2
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Val Arg Lys Phe Lys Lys Thr Cys Leu Ile Val Ser Ser Leu Leu
1               5                   10                  15

Ala Cys Ser Gly Leu Ala Tyr Ser Glu Asp Ser Pro Gln Val Val Ser
            20                  25                  30

Gln Gly Gly Pro Leu Gly Ala Thr Ser Ile Gly Asp Gln Asn Leu Gly
        35                  40                  45

Gln Pro Asp Pro Asn Ala Ser Gly Ala Ser Ser Thr Thr Gln Thr Thr
    50                  55                  60

Gly Ser Asn Leu Asn Asp Arg Glu Leu Leu Lys Leu Gln Gln Gln
65                  70                  75                  80

Val Gln Gln Leu Gln Gly Gln Leu Gln Gln Leu Lys Ala Gln Gly Asn
                85                  90                  95

Gly Gly Gly Leu Gln Asn Thr Tyr Asn Gly Ser Ser Gln Phe Thr Thr
            100                 105                 110

Tyr Ser Ser Lys Val Asp Gly Asn Lys Asn Pro Arg Thr Leu Gly Gly
            115                 120                 125

Asn Gly Glu Ser Lys Asp Leu Ser Gln Ala Leu Ile Gly Gly Gln Thr
        130                 135                 140

Ser Ser Asp Ile Met Gly Asn Val Asn Ala Ser Asn Ser Ile Ile Asn
145                 150                 155                 160

Leu Ala Ser Glu Pro Leu Gly Gly Val Phe Asn Gln Lys Gly Gly Ile
                165                 170                 175

Asp Val Gly Gly Ala Pro Ala Ile Thr Thr Gln Gly Gln Val Thr Tyr
            180                 185                 190

Leu Gly Ser Tyr Ser Gly Asn Asn Ser Ile Pro Ile Gly Gln Ile Ser
        195                 200                 205

Ser Asn Leu Phe Ala Ser Thr Leu Leu Gly Gln Arg Glu Lys Phe Asp
    210                 215                 220

Asp Tyr Ser Val Phe Phe Gly Gly Phe Ile Glu Ala Asp Ala Gln Ala
225                 230                 235                 240

Trp Phe Gly Ser Ala Val Thr Lys Val Gln Asn Ala Gly Gln Leu Ser
                245                 250                 255

Ser Asn Gly Gln Asn Ile Tyr Leu Thr Ser Ala Asn Leu Tyr Phe Leu
            260                 265                 270

Ser Asn Leu Gly His Tyr Val Thr Ala Gln Phe Asp Phe Asp Thr Asn
        275                 280                 285

Glu Ser Gly Ser Phe Ser Leu Gly Asn Ala Phe Val Ile Phe Gly Asn
    290                 295                 300

Leu Asp Ile Ser Pro Phe Phe Val Thr Ala Gly Arg Asn Lys Leu Ser
305                 310                 315                 320

Val Gly Ser Tyr Gly Gly Gly Gly Thr Trp Thr Ser Gly Ile Thr Lys
```

```
                    325                 330                 335
Phe Leu Ser Pro Asn Gln Val Thr Asn Val Ser Ile Asp Tyr Lys Asp
                340                 345                 350

Gln Val Trp Asn Ala Asn Ile Ala Val Phe Gly Ser Asp Asp Arg Arg
                355                 360                 365

Ala Asn Phe Ser Thr Gly Leu Phe Tyr Ala Asp Ser Trp Thr Pro Asn
        370                 375                 380

Leu Ala Ala Gly Phe Asn Val Gly Tyr Val Phe Asn Ile Ala Gly Ala
385                 390                 395                 400

Gly Asn Ser Ser Ile Ala Asn Ser Leu Ala Asn Leu Asn Arg Ser Ser
                405                 410                 415

Asp Asn Val Gly Ala Leu Asn Val Asp Gly Asn Leu Thr Tyr Ala Ile
                420                 425                 430

Trp Asp Gly Phe Leu Asn Leu Gly Ala Gly Trp Ala Ser Thr Thr Thr
                435                 440                 445

Lys Glu Asp Phe Asn Asn Asn Gly Gly Ser Val Leu Ala Gly Ala Trp
        450                 455                 460

Tyr Gly Ala Leu Asn Tyr Ser Ala Ile Leu Gly Gly Arg Asn Thr Asn
465                 470                 475                 480

Phe Gly Val Thr Tyr Gly Gln Ser Tyr Asn Ala Ala Ile Pro Met
                485                 490                 495

Glu Thr Ala Asn Ala Ser Pro Thr Phe Gly Gln Thr Ala Ser Gly Ile
                500                 505                 510

Lys Gln Gln Leu Ile Phe Ser Ala Gln Arg Ala Tyr Phe Asp Asp Asn
                515                 520                 525

Val Leu Phe Gly Pro Glu Tyr Ala Tyr Gln Arg Leu Tyr Thr Gly Glu
        530                 535                 540

His Met Asn Thr Ile Thr Leu Asp Met Ser Val Tyr Val
545                 550                 555

<210> SEQ ID NO 3
<211> LENGTH: 481
<212> TYPE: PRT
<213> ORGANISM: Francisella tularensis

<400> SEQUENCE: 3

Met Phe Arg Lys Lys Leu Leu Val Leu Ile Thr Ile Leu Phe Phe Phe
1               5                   10                  15

Leu Asn Thr Ser Tyr Ala Val Val Asn Gln Val Asn Asn Ser Gln Gln
                20                  25                  30

Leu Asp Ala Asn Glu Val Ser Lys Leu Ala Lys Glu Ile Lys Leu Leu
            35                  40                  45

Gln Ala Gln Ile Ala Asn Leu Asp Thr Gln Lys Ile Thr Asp Asp Ile
        50                  55                  60

Val Val Gly Leu Gly Ser Gln Gln Lys Val Ser Asn Asp Gln Phe Asn
65                  70                  75                  80

Asp Phe Asp Lys Ser Thr Lys Val Arg Glu Gln Tyr Leu Gln Gln Gln
                85                  90                  95

Val Ser Leu Ser Ser Asp Asp Arg Glu Val Asp Val Gly Asn Gln
                100                 105                 110

Val Lys Ile Thr Thr Gln Gly Glu Ile Ser Tyr Val Gly Ser Phe Ser
            115                 120                 125

Ser Asn Asn Thr Val Pro Ile Gly Gln Leu Pro Ser Asn Leu Phe Ala
        130                 135                 140

Ser Ser Ile Leu Arg Gln Arg Ala Phe Phe Asp Asp Tyr Ser Ile Phe
```

-continued

```
145                 150                 155                 160
Phe Gly Gly Phe Ile Gln Ala Asp Ala Gln Ile Trp Asn Gly Thr Asp
                165                 170                 175
Ile Thr Thr Arg Asn Gly Gly Asn Phe Thr Gly Asn Gly Glu Asn Ile
                180                 185                 190
Tyr Leu Thr Ser Ala Thr Leu Tyr Phe Leu Ala Asn Leu Gly His Tyr
            195                 200                 205
Val Thr Ala Asn Leu Asp Phe Val Ala Asn Gln Asn Asn Tyr Asp
        210                 215                 220
Leu Gln Asp Ala Phe Val Ile Phe Gly Asn Leu Asp Thr Thr Pro Val
225                 230                 235                 240
Phe Val Ser Val Gly Lys Tyr Arg Pro Ser Val Gly Ser Phe Gly Gly
                245                 250                 255
Gly Gly Pro Trp Thr Ser Gly Ile Thr Ala Asn Met Phe Arg Pro Leu
                260                 265                 270
Arg Val Thr Asn Ala Ala Ile Asn Tyr Arg Gly Asp Thr Ser Asn Ala
                275                 280                 285
Asn Phe Thr Val Phe Asp Ala Lys Asn His Ala Thr Phe Ser Val Ala
            290                 295                 300
Tyr Phe Asp Ala Val Ser Ile Pro Asn Ile Ala Gln Val Gly Phe Asn
305                 310                 315                 320
Leu Gly Tyr Met His Asp Ile Arg Gly Ala Asn Asn Arg Phe Asn Phe
                325                 330                 335
Ile Asp Lys Arg Val Gly Glu Phe Asn Ile Asp Thr Ala Ile Ser Phe
                340                 345                 350
Glu Ser Ile Pro Phe Leu Pro Gly Asn Leu Asn Val Gly Ala Gly Trp
            355                 360                 365
Ala Thr Thr Thr Thr Gln Ser Thr Gln Phe Asn Gly Arg Ser Asn Ala
        370                 375                 380
Phe Ala Gly Ala Phe Thr Val Gln Ala Ala Tyr Thr Phe Lys Leu Phe
385                 390                 395                 400
Gly Ser Gly Gln Asn Ile Asn Ala Ser Tyr Gly His Ser Tyr Asn Ala
                405                 410                 415
Asp Asn Ile Pro Met Pro Leu Ser Ala Gly Gly Ser Phe Phe Leu Ala
                420                 425                 430
Ala Ser Gly Ile Lys Asp Gln Ile Leu Val Ser Thr Gln Arg Ser Phe
            435                 440                 445
Phe Asp Asp Asn Val Leu Ile Gly Pro Glu Tyr Ser Trp Gln Ser Leu
        450                 455                 460
Tyr Asn Gly Gln Arg Met Asn Thr Leu Thr Leu Asp Leu Ser Val Tyr
465                 470                 475                 480
Ile
```